United States Patent [19]
Lizardi et al.

[11] Patent Number: 5,652,107
[45] Date of Patent: Jul. 29, 1997

[54] DIAGNOSTIC ASSAYS AND KITS FOR RNA USING RNA BINARY PROBES AND A RIBOZYME LIGASE

[75] Inventors: Paul M. Lizardi, Colonia Rancho Cortez Cuernavaca, Mexico; Sanjay Tyagi, New York, N.Y.; Ulf D. Landegren, Uppsala, Sweden; Fred R. Kramer, Riverdale, N.Y.; Jack W. Szostak, Boston, Mass.

[73] Assignee: The Public Health Research Institute of the City of New York, Inc., New York, N.Y.

[21] Appl. No.: 683,045

[22] Filed: Jul. 15, 1996

Related U.S. Application Data

[63] Continuation of Ser. No. 315,191, Sep. 29, 1994, abandoned, which is a continuation of Ser. No. 5,893, Jan. 15, 1993, abandoned.

[51] Int. Cl.$^6$ .............. C12Q 1/68; C12P 19/34; C07H 21/04
[52] U.S. Cl. .............. 435/6; 435/5; 435/91.1; 435/91.2; 435/91.3; 536/24.5
[58] Field of Search .............. 435/5, 6, 91.1, 435/91.2, 91.3; 536/24.5

[56] References Cited

U.S. PATENT DOCUMENTS 4,988,617  1/1991  Landegren et al. .............. 436/6

FOREIGN PATENT DOCUMENTS 481704  4/1992  European Pat. Off. .......... C12Q 1/68
9212261  7/1992  WIPO .............. C12Q 1/68

OTHER PUBLICATIONS

HJ Blok "Target-dependent Amplifiable Nucleic Acid Hybridization Probes," a thesis published later than Jan. 19, 1992.

Stratagene catalog (1988), p. 39.

Barany, F., Genetic Disease Detection and DNA Amplification Using Cloned Thermostable Ligase. Proc. Natl. Acad. Sci. U.S.A., 1991; 88:189–193.

Doudna, J.A. and Szostak, J.W. RNA–Catalysed Synthesis of Complementary–Strand RNA. Nature, 1989; 339:519–522.

Doudna, J.A., Couture, S., Szostak, J.W., A Multisubunit Ribozyme That is a Catalyst of and Template for Complementary Strand RNA Synthesis. Science, 1991; 251:1605–1608.

Erlich, H.A., Gelfand, D. and Sninsky, J.J., Recent Advances in the Polymerase Chain Reaction. Science, 1991; 252:1643–1651.

Green, R., Ellington, A., Szostak, J.W., In Vitro Genetic Analysis of the Tetrahymena Self–Splicing Intron. Nature, 1990; 347:406–408.

Fareed, G.C., Wilt, E.M., and Richardson, C.C. (1971) Enzymatic Breakage and Joining of Deoxyribonucleic Acid. The Journal of Biol. Chm. 1971; 4:925–932.

Green, R. and Szostak, J.W., Selection of a Ribozyme that Functions as a Superior Template in a Self–Copying Reaction. Science, 1992; 258–1910–1915.

(List continued on next page.)

*Primary Examiner*—George C. Elliott
*Assistant Examiner*—Jeffrey Fredman
*Attorney, Agent, or Firm*—Fish & Richardson P.C.

[57] ABSTRACT

There are provided nucleic acid hybridization assays for RNA targets using RNA binary probes and a ribozyme ligase that is a stringent RNA-directed RNA ligase. Preferred assays include exponential amplification for signal generation. Tetrahymena ribozyme ligase is a preferred ligase for use in this invention. It may be tethered to hold it close to the ligation junction. One assay according to this invention is a "tethered ligase chain reaction." Also provided are kits for performing assays according to the invention.

35 Claims, 4 Drawing Sheets

OTHER PUBLICATIONS

Hunsaker, W.R., Badri, H., Lombardo, M., and Collins, M.L., Nucleic Acid Hybridization Assays Employing dA–Tailed Capture Probes. II. Advanced Multiple Capture Methods. Anal. Biochem. 1989; 181:360–370.

Kleppe, K., van de Sande, J.H., and Khorana, H.G. Polynucleotide Ligase–Catalyzed Joining of Deoxyribo–oligonucleotides on Ribopolynucleotide Templates and of Ribo–ogligonucleotides on Deoxyribopolynucleotide Templates. Proc. of Natl Acad. of Sci., 1970, 67/1:68–73.

Landegren, U., Kaiser, R., Sanders, J., and Hood, L., A Ligase–Mediated Gene Detection Technique. Science, 1988; 241:1077–1080.

Lizardi, P.M., Guerra, C.E., Lomeli, H., Tussie–luna, I., and Kramer, F.R., Exponential Amplification of Recombinant–RNA Hybridization Probes. Biotechnology, 1988; 6:1197–1202.

Lomeli, H., Tyagi, S., Pritchard, C.G., Lizardi, P.M., and Kramer, F.R., Quantitative Assays Based on the Use of Replicatable Hybridization Probes. Clin. Chem., 1989; 35/9:1826–1831.

Michel, F., Hanna, M., Green, R., Bartel, D.P., and Szostak, J.W., The Guanosine Binding Site of the Tetrahymena Ribozyme. Nature, 1989; 342:391–395.

Moore, Melissa J., and Sharp, Phillip A. Site–Specific Modification of Pre–mRNA: The 2'–Hydroxyl Groups at the Splice Sites. Science, 1992, 256:992–997.

Morrissey, D.V., Lombardo, M., Eldredge, J.K., Kearney, K.R., Groody, E.P., and Collins, M.L., Nucleic Acid Hybridization Assays Employing dA–Tailed Capture Methods. Anal. Biochem., 1989, 181:345–359.

Pritchard, C.G., and Stefano, J.E., Amplified Detection of Viral Nucleic Acid at Subattomole Levels Using Q beta Replicase. Ann. Biol. Clin. (Paris), 1990; 48:492–497.

Pritchard, C.G., and Stefano, J.E. (1991) Detection of Viral Nucleic Acids by QB Replicase Amplification. Medical Virology 10 (de la Maza, L.M., and Peterson, E.M., eds), pp. 67–80, Plenum Press, New York.

Sano, H. and Feix, G. Ribonucleic Acid Ligase Activity of Deoxyribonucleic Acid Ligase From Phage T4 Infected Escherichia coli. Biochemistry, 1974, 13/25;5110–5115.

Strobel, S.A., and Cech, T.R., Efficient Ligation of a Highly Structured RNA using T4 DNA Ligase. U.S. Biochem. Corp., 1992, 19/3;89–91.

Tyagi, U.S. Patent Appln. Ser. No. 08/004,993, filed Jan. 15, 1993, for Diagnostic Assays and Kits For RNA Using RNA Binary Probes and a Protein That is An RNA–Directed RNA Ligase.

Tyagi, et al. U.S. Patent Appln. Ser. No. 08/006,073, filed Jan. 15, 1993, for Sensitive Nucleic Acid Sandwich Hybridization Assays and Kits.

CAPTURE PROBE 35

```
           10         20         30         40         49
5' BIOTIN-TACGACTGCT ACCAAGATAA CTTTTCCTTC TAAAATGTGTA CAATCTAGC 3'
         |||||||||| |||||||||| |||||||||| |||||||||| |||||||||
```

CAPTURE PROBE 36

```
           10         20         30         40         49
5' BIOTIN-TACGATGTCT GTTGCTATTA TGTCTACTAT TCTTTCCCCT GCACTGTAC 3'
         |||||||||| |||||||||| |||||||||| |||||||||| |||||||||
```

FIG. 3

INCUBATE TARGET WITH PROBES 61-64
TO HYBRIDIZE PROBES 61, 62

LIGATE PROBES 61, 62
MELT
HYBRIDIZE PROBES 63, 64

LIGATE PROBES 63, 64
MELT
HYBRIDIZE PROBES 61, 62

CYCLE 20-30 TIMES

DIAGNOSTIC ASSAYS AND KITS FOR RNA USING RNA BINARY PROBES AND A RIBOZYME LIGASE

This application is a continuation of application Ser. No. 08/ 315,191 filed on Sep. 29, 1994, now abandoned, which is a continuation of Ser. No. 08/005,893, filed Jan. 15, 1993 now abandoned.

This invention was made with government support under grant number HL-43521 awarded by the National Institutes of Health. The United States government has certain rights in this invention.

This invention relates to nucleic acid hybridization assays for the detection of RNA. Such assays are broadly applicable to diagnosis of a disease or condition in humans or animals, assays for pathogens in biological samples, and assays for an organism or virus in food, agricultural products or the environment.

BACKGROUND OF THE INVENTION

Nucleic acid hybridization assays of various types are known. There are several assays that utilize a pair of DNA probes and a step of ligating the probes with a DNA ligase, wherein ligation requires that the probes be hybridized adjacent to one another on a target. In this application we use the term "binary probes assay" to refer generally to any assay that includes the step of ligating a pair of probes that are hybridized to a nucleic acid target adjacent to one another. The requirement that the pair of probes be hybridized only when adjacent to one another on a target means that ligation is "target-dependent." We refer to the pair of probes as "binary reporter probes" or "binary probes."

One binary probe assay is the ligase chain reaction ("LCR") (Barany, 1991). In LCR, a first pair of DNA binary probes is hybridized to one complementary strand of a DNA target and ligated there by a DNA-directed DNA ligase to form a first ligated product, and a second pair of DNA binary probes is hybridized to the first ligated product and similarly ligated to form a second ligated product. By cycling the reaction temperature, steps of melting, annealing probes and ligation are repeated to produce exponentially amplified product, i.e., ligated probes, that are then detected. We sometimes refer to ligated probes as a "reporter molecule" to distinguish from probes per se.

Another binary probe assay for DNA targets utilizes a pair of DNA binary probes, one of which serves to immobilize the target on the surface of a solid and the other of which contains a radioactive atom or fluorescent moiety (Landegren et al., 1988). This assay is reported to apply to RNA targets (using DNA binary probes), but no examples are given (Landegren & Hood, 1991).

A third assay for DNA targets utilizes a pair of DNA binary probes, one of which serves to immobilize the target on the surface of a solid, wherein the reporter molecule is a template that permits exponential amplification by an RNA-directed RNA polymerase such as bacteriophage Qβ replicase (Martinelli et al., 1992). The reporter molecule may be a DNA molecule that is itself a template for Qβ replicase (direct amplification), or it may be template for transcription by T7 RNA polymerase to produce an RNA template for Qβ replicase (indirect amplification).

The assays described above suffer from several drawbacks pertinent here. Most are for DNA targets, for example. That is a drawback, because RNA targets suitable for detection are in most cases much more abundant in samples than their corresponding DNA targets. All of the above assays use DNA binary probes. LCR requires thermal cycling and a thermocycler for amplification, and requires product analysis such as gel electrophoresis. The DNA binary probe assays of Landegren et al., 1988 and Landegren & Hood, 1991 do not include amplification and, therefore, are not sensitive assays. In assays employing exponential amplification by Qβ replicase (Martinelli et al, 1992) the use of DNA probes limits sensitivity: either an additional step of transcription is required, which increases cost, takes additional time, and lowers sensitivity, or a DNA reporter molecule must be amplified directly, which is very inefficient, thereby lowering sensitivity.

It is an objective of this invention to overcome the limitation of existing binary probe assays that use DNA binary probes.

It is a further objective of this invention to enable sensitive binary-probe assays for RNA targets using RNA probes and a stringent RNA-directed RNA ligase.

SUMMARY OF THE INVENTION

The assays of this invention are nucleic acid hybridization assays for RNA targets using RNA binary probes and an RNA-directed RNA ribozyme ligase that is stringent against hybridization mismatches between the probes and the target. By "stringent" it is meant that at least 10-fold to 100-fold less ligation occurs if there are as few as two base-pair mismatches between the binary probes and the target within nine nucleotides of the ligation junction.

Preferred embodiments include sandwich hybridization assays.

Preferred embodiments are assays that include exponential amplification for signal generation, including amplification of an RNA reporter molecule at a single temperature by an RNA-directed RNA polymerase, such as Qβ replicase (Lizardi et al., 1988; Lomeli et al., 1989; Martinelli et al., 1992) or amplification of an RNA target with temperature cycling, such as by the ligase chain reaction (Barany, 1991). Especially preferred embodiments also use techniques for reducing background in the assay, such as, for example, reversible target capture (Morrissey et al., 1989; Hunsaker et al., 1989), or one or more of the background reduction techniques disclosed in U.S. patent application Ser. No. 08/006,073, for Sensitive Nucleic Acid Sandwich Hybridization Assays and Kits, filed on the same day as the instant application by S. Tyagi, U. Landegren, P. Lizardi and F. Kramer (hereinafter "Tyagi et al.").

The assays of this invention utilize a stringent RNA-dependent ribozyme ligase for ligation, most preferably a modified Tetrahymena ribozyme ligase disclosed in the literature (Doudna & Szostak, 1989). We have discovered a way to use this ribozyme ligase to ligate binary probes having a combined nucleotide probe sequence length (that is, the combined number of nucleotides hybridized to the target) appropriate for hybridization assays, that is, minimally 24 and up to about 45 nucleotides, preferably in the range of 36–42 nucleotides.

Preferred embodiments of this invention utilize a ribozyme ligase that is tethered. As used here, "tethered" means held in proximity to its point of operation. A tethered ribozyme ligase is an RNA comprised of three regions: (1) a ribozyme ligase sequence; (2) a "holdfast," which is a sequence complementary to the target or a complement thereof; and (3) a "tether," which is a spacer, a sequence that links the ribozyme ligase sequence to the holdfast. The Examples illustrate two preferred embodiments of a tethered ribozyme ligase. In one embodiment the holdfast is a sequence hybridizable to the target at a site near the target sequence, typically 25–50 nucleotides removed from the ligation point, and the tether is a short sequence covalently linked on one end to the holdfast and on the other end to the ribozyme sequence. In this embodiment a stable holdfast 20–35 nucleotides long and a short tether of 5–12 nucleotides are preferred. In another embodiment, used in an assay that we call the "tethered ligase chain reaction" (TLCR), a short tether sequence is covalently linked on one end to the ribozyme sequence and on the other end to a binary reporter probe, which in this case acts as the holdfast. In this case a short tether of 5–12 nucleotides is also preferred. In either embodiment, if the tether is too short, the ribozyme ligase sequence will not be able to ligate the binary probes, but if the tether is too long, the improvement in ligation efficiency will be reduced. A suitable tether length for a particular application can be readily ascertained by trial and error.

Ribozymes useful in assays according to this invention may contain natural nucleotides or modified nucleotides, such as 2'-O-methylribonucleotides, or both.

We have developed a straightforward test procedure to identify ribozyme ligases useful in this invention.

This invention also includes diagnostic kits for preselected targets containing a pair of RNA binary probes, a ribozyme ligase, and instructions for performing an assay according to this invention. Additional reagents may be included in preferred kits.

A detailed description of preferred embodiments of this invention, including particularly preferred embodiments, follows in the Detailed Description. Neither the Detailed Description nor the examples are intended to limit the scope of this invention or the appended claims.

BRIEF DESCRIPTION OF THE DRAWINGS

FIG. 3 shows the capture probes (SEQ ID NOS: 11–12) of Example 5.

DETAILED DESCRIPTION

Figure 1:
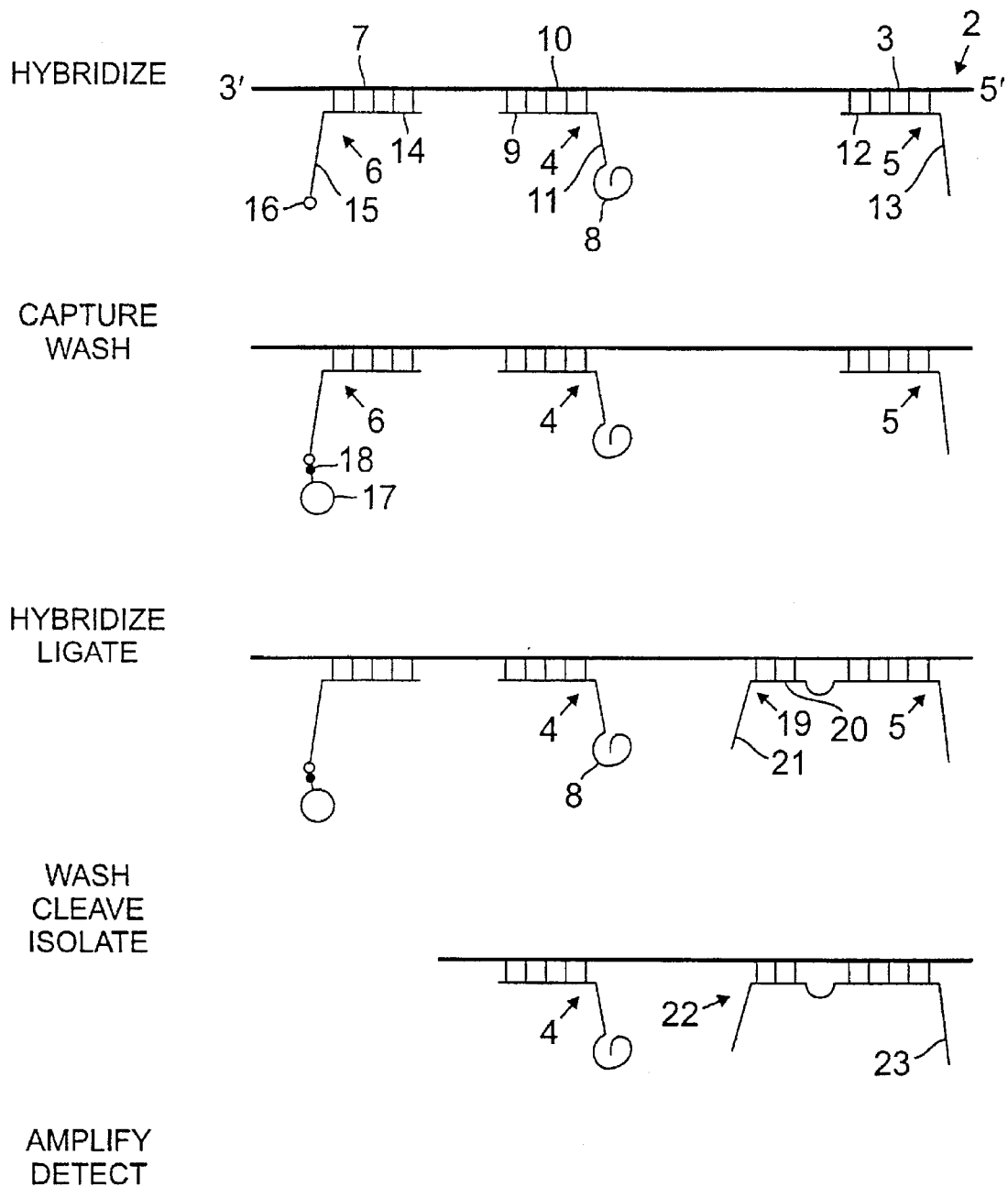
FIG. 1 depicts the assay of Example 4.

Straightforward tests can be used to determine whether or not a particular ribozyme ligase has the dual properties of stringency and RNA template-directed catalytic activity necessary for use in assays according to this invention. Using the tests described in Example 1, we discovered that the Tetrahymena ligase of Doudna & Szostak (1989) is a suitable ligase, if the "first probe" contains a probe sequence (the nucleotide sequence that hybridizes to target RNA) that is as long as nine nucleotides but not if it is 12-nucleotides long or longer. To ensure specificity to the target sequence, we made the probe sequence of the "second probe" twenty-eight nucleotides long, thereby providing a combined probe sequence length of thirty-seven nucleotides. This ribozyme ligase does not work with a pair of probes having probe sequences of approximately equal length of twelve nucleotides or more. The combined probe sequences should be at least about 25 nucleotides in length, preferably 36–42 nucleotides. We also determined that, where used at its optimal ligation temperature of 58° C., this ligase was stringent against two hybridization mismatches. We also determined that neither the "first probe" nor the "second probe", both of which contained a portion of MDV-1 RNA, a template for Qβ replicase, was exponentially amplified by Qβ replicase in the presence of 0.5 µg/ml propidium iodide (See Pritchard & Stefano, 1991). In sum, we discovered RNA binary probes and conditions suitable for the hybridization assays of Examples 2 and 3 at which this particular ribozyme ligase functioned as an RNA-directed RNA ligase.

Using the stringency test described in Example 1, we demonstrated that another ribozyme ligase, the SunY-td ligase described by Doudna et al. (1991), when used at its optimal ligation temperature of 45° C., did give some ligation with two mismatches and is unsatisfactory for use in assays according to this invention. Other embodiments of this invention may be implemented, however, by using an improved SunY-derived mutant ribozyme ligase capable of catalyzing ligation at high temperature and lower salt and magnesium concentration. Such a mutant ribozyme can be isolated by using appropriate selection conditions in an in vitro directed evolution experiment similar to that described by Green et al. (1990) and Green & Szostak (1992). Selections would be carried out as described in these papers, except that the ligation temperature would be 58° C. instead of 45° C. Mutants selected in this fashion may satisfy the ligation stringency test of Example 1 because of the higher ligation temperature. Likewise, appropriate in vitro directed evolution experiments can be used to isolate an improved Tetrahymena mutant ribozyme capable of ligating binary probes in assays where the hybrid formed by the left probe (the probe donating a 3'-hydoxyl at the ligation junction) is longer than 9 nucleotides.

The assays of this invention are for RNA targets. They require RNA binary probes and a stringent ribozyme ligase. With those restrictions, any appropriate assay protocol can be used. The ligated product, here referred to as an RNA "reporter molecule," may itself be detected, i.e., without being amplified, in assays analogous to known assays using DNA binary probes (Landegren et al., 1988; Landegren and Hood, 1991). Alternately, the RNA binary probes may be designed such that the reporter molecule produced by their ligation is amplifiable, i.e., a template for an RNA-directed RNA polymerase, such as Qβ replicase (see Lizardi et al., 1988; Lomeli et al., 1989; Pritchard and Stefano, 1991; Martinelli et al., 1992, for examples of appropriate RNA molecules).

The assays of this invention may utilize one of the RNA binary reporter probes to immobilize target molecules on a solid surface, analogously to several of the above references that do so for DNA probes.

Preferred assays according to this invention utilize exponential amplification of RNA reporter molecules by an RNA-directed RNA polymerase or exponential amplification of RNA targets by LCR, as described above. In addition, preferred embodiments of assays according to this invention utilize techniques for reducing background, such as, for example, reversible target capture (Morrissey et al., 1989; Hunsaker et al., 1989).

Preferred embodiments of assays according to this invention utilize one or both of the background reduction techniques disclosed in Tyagi et al., U.S. patent application Ser. No. 08/006,073, which is incorporated herein by reference. The background reduction techniques are (1) the use of a separate capture probe, hybridizable to the target at a site different from the target sequence to which the binary reporter probes hybridize, to form capture probe-target-reporter probes hybrids, immobilization of those hybrids, and (2) release of reporter probes-target hybrids from the capture probes by cleavage, as by ribonuclease H (RNase H).

As stated earlier, this invention also includes kits for performing assays according to this invention. A preferred kit for sandwich assays may contain some or all of the following items:

1. 5M guanidine thiocyanate (GuSCN) for the lysis of cells in clinical samples;
2. A mixture containing RNA binary reporter probes for a preselected RNA target and, preferably, DNA capture probes;
3. A solid, such as a dipstick, reaction tube or paramagnetic particles, with streptavidin covalently bound thereto;
4. A magnetic separation device;
5. Nucleotides;
6. A ribozyme ligase useful in this invention, preferably Tetrahymena ligase;
7. RNase H and Qβ replicase;
8. Buffers for ligation and amplification;
9. Reagents for detecting the amplified reporters, such as radioactive alpha-$P^{32}$-cytidine triphosphate or propidium iodide;
10. Instructions for performing an assay according to this invention.

A bare kit may contain only items 2, 6 and 10. A more complete kit will also contain at least items 1, 3 and 7. A kit containing at least items 1-2 and 5-10, where the solid is a dipstick or reaction tube, is particularly useful for assays to be performed outside a well-equipped laboratory.

A preferred kit for a ligase chain reaction assay may contain some or all of the following items:

1. 5M GuSCN;
2. Two pairs of RNA LCR probes for a preselected RNA target;
3. Tetrahymena ribozyme ligase, preferably tethered to one of each pair of RNA LCR probes;
4. Capture probe, preferably DNA, and a cleaving agent, preferably ribonuclease H;
5. Paramagnetic particles or other solid to which streptavidin covalently linked;
6. LCR buffer; and
7. Instructions.

A complete kit for performing a tethered ligase chain reaction will contain all of items 1-7. A base kit will contain items 2, 3 and 7, but preferably also item 4.

EXAMPLE 1

This example describes the tests we have used to ascertain whether or not a particular ribozyme ligase is suitable for use in this invention. For illustrative purposes, the tests are described for Tetrahymena ribozyme ligase, a ribozyme ligase that we have discovered to be suitable for use in assays of this invention, if the nucleotide probe sequences of a pair of RNA binary probes are restricted in the manner described. The stringency test we used is as follows:

(1) An artificial RNA target with a known sequence of 18 nucleotides is synthesized by transcription or obtained from commercial sources.
(2) A pair of RNA binary probes complementary to this target are synthesized by transcription and purified by acrylamide gel electrophoresis, or obtained from commercial sources. The first RNA probe contains 9 nucleotides and is complementary to the last 9 nucleotides of the artificial target. This probe length was chosen, because it is about the maximum probe section length for a probe useful in this invention. The second RNA probe contains 10 nucleotides, beginning with a guanosine at the 5'-end, and followed by 9 nucleotides complementary to the first 9 nucleotides of the artificial target. We note that there are mutant ribozymes for which the 5' guanosine would be replaced by 2-aminopurine, a technique reported to improve specificity of ligation (Michel et al., 1989). The first probe is labeled at the 5'-end with radioactive phosphorous using polynucleotide kinase.

(3) A modified version of the second probe is synthesized which contains a guanosine at the 5'-end, followed by 9 nucleotides of which only 7 can base pair with the target. Two nucleotides, located at internal positions in the sequence, form mismatches with the target sequence.

(4) A ligation assay is carried out in ligation buffer (which contains 30 mM Tris-HCl, pH 7.5, 10 mM $NH_4Cl$, 20 mM $MgCl_2$, 4 mM spermidine). Labeled first probe and unlabeled second probe are incubated at 58° C. for 3 hours in the presence of artificial target RNA and Tetrahymena ribozyme ligase. If ligation occurs, ligation product 18-nucleotides in length is obtained. To see if ligation occurred, the "product" is assayed by polyacrylamide gel electrophoresis and radioautography.

In parallel experiments using in one case labeled first probe and unlabeled second probe and in the other case labeled first probe and modified (mismatched) second probe with Tetrahymena ribozyme ligase, an 18-nucleotide ligation product was found only for the former. Thus, Tetrahymena ribozyme ligase is a stringent ribozyme ligase that shows very little ligation when there is no mismatch at the ligation junction but there are 2 mismatches within nine nucleotides of the junction. Or course, mismatches other than a U:G wobble base-pair at the ligation junction are not tolerated. A relatively high-ligation temperature, and a relatively low salt concentration in the ligation buffer, contribute to stringency.

Similar tests with longer artificial targets are then used to ascertain whether or not a particular ribozyme ligase has the required ligation activity for a pair of probes having a combined probe sequence length appropriate for assays according to this invention. (We ascertained that Tetrahymena ribozyme ligase does not ligate a pair of RNA probes both twelve nucleotides in length.) As stated above, we discovered that Tetrahymena ribozyme ligase does not work when a satisfactory combined hybridization length is split about evenly between the two binary probes, but we discovered that it can be made to work practically when one probe has the minimum probe sequence nine nucleotides long and the other probe has a compensatingly long probe sequence to impart overall specificity to the target sequence. Optimum ligation conditions can be investigated simultaneously, as will be apparent to one skilled in the art.

Also, similar tests with artificial targets can be used to ascertain the effectiveness of tethering ribozyme ligases, as well as to determine the optimal length of the tether.

EXAMPLE 2

This example describes the preparation of a "first probe" and a "second probe" used in several of the examples that follow, as well as the preparation of a tethered ribozyme ligase used in two examples.

The "first probe" is a 71 nucleotide-long RNA generated by in vitro transcription of an artificial gene. The sequence of this RNA is as follows:

5'-GGGGACCCCCCCGGAAGGGGGGGACGAGGUGC GGGCACCUCGUACGGGAGUUCGAGCGUGAC <u>GACCGUAGU</u>-3' (SEQ ID NO: 1). The last 9 nucleotides of this RNA form a "first probe sequence" (underlined) that is complementary to the sequence 3'-UUGGCAUCG-5' (SEQ ID NO: 3), which is part of the HIV-1 RNA target sequence. The "first probe sequence" ends with a U, which will pair with a G on the target sequence, thus forming a U:G wobble base-pair. This is a preferred substrate for the Tetrahymena ribozyme ligase and results in enhanced ligation activity. Alternatively, as long as spermidine is present in the ligation buffer, any Watson-Crick base-pair can be used at the ligation junction, with only moderately decreased activity (Doudna & Szostak, 1989).

The "second probe" is a 186-nucleotide-long RNA with the sequence (SEQ ID NO: 2):
5'-<u>GACUGGUGAAAUUGCUGCCAUUGUCUGUA</u>GCA CGCGCUAGCGCUUUCGCGCUCUCCCAGGUG ACGCCUCGUGAAGAGGCGCGACCUUCGUGCGU UUCGGCAACGCACGAGAACCGCCACGCUGCUU CGCAGCGUGGCUCCUUCGCGCAGCCCGCUGCG CGAGGUGACCCCCCG AAGGGGGGUUCCC-3'.
The first nucleotide of this RNA is a guanosine, which does not pair to HIV-1 RNA, but is required for ligation by the Tetrahymena ribozyme ligase (Doudna & Szostak, 1989). The next 28 nucleotides form a "second probe sequence" (underlined) that is complementary to the sequence (SEQ ID NO: 4)
3'-UGACCACUUUAACGACGGUAACAGACAU-5', which is the other part of the HIV-1 RNA target sequence adjacent to the 5' end of sequence 3'-UUGGCAUCG-5' (SEQ ID NO: 3).

The second probe is generated by in vitro transcription of an artificial gene that codes for the desired RNA sequence and contains a T7 promoter. The artificial gene is generated by the polymerase chain reaction using the following primers:
5'-TGCGTAATACGACTCACTATAGACTGGTGAAATT GCTGCCATTGTCTGTAGCACGCTGCTAGCGCTTT CGCGCTCTCC-3' (SEQ ID NO: 5) and 5' GGGGAAC- CCCCCTTCGGGGGGTCACC 3' (SEQ ID NO: 6). These primers are used in a polymerase chain reaction in the presence of plasmid pT7MDVHIV20, described at page 1827 of Lomeli et al., 1989, to generate the artificial gene for the synthesis of the second probe. The 186-nucleotide-long transcript is purified by polyacrylamide gel electrophoresis.

The tethered ribozyme ligase is generated by in vitro transcription, as described by Doudna & Szostak (1989). An artificial gene for the transcription of the tethered ribozyme ligase is generated by PCR from plasmid pJD1100 (Doudna & Szostak, 1989) using the following primers:
5'-GCGTAATACGACTCACTATAGGGTTTTTACTGGCC ATCTTCCTGCTAATTTTAAGTTGAGAG TTATCAGGCATGCACCTG-3' (SEQ ID NO: 7) and 5'-CTAGCTCCCATTAAGGAGAG-3' (SEQ ID NO: 8). The product of in vitro transcription is 345 nucleotides long and contains a holdfast having the sequence (SEQ ID NO: 9)
5'-GTTTTTACTGGCCATCTTCCTGCTAATTTTAA-3' and a tether having the sequence 5'-TTTGAG3' (SEQ ID NO: 10), which is connected to the P2 stem of the Tetrahymena ribozyme ligase (Doudna & Szostak, 1989). The holdfast is complementary to a sequence in HIV-1 RNA that is five nucleotides removed from the target sequence.

Each binary probe was tested to see if it could be exponentially replicated by incubation with Qβ replicase in the presence of 0.5 μg/ml of propidium iodide, and neither was.

EXAMPLE 3

This embodiment is a nucleic acid sandwich hybridization assay for HIV-1 RNA employing "first probe" and "second probe" as described in Example 2, in conjunction with the Tetrahymena ribozyme ligase of Doudna & Szostak (1989) in a non-tethered form. The assay uses a capture probe (Lomeli et al., 1989) and a form of reversible target capture (see, Morrissey et al., 1989; Munsaker et al., 1989 for details of reversible target capture). It also includes exponential amplification of signal.

The protocol for this particular assay is as follows:
(1) A sample, blood containing MIV-1-infected cells, is dissolved in 50 μl of 5M guanidine thiocyanate (GuSCN), 80 mM EDTA. After lysis the second probe and a suitable oligo-(dA)-tailed capture probe capable of binding the RNA target (Lomeli et al., 1989) are added.
(2) The mixture is incubated for a period of 30 minutes at 37° C. to allow solution hybridization to proceed.
(3) Paramagnetic particles containing short oligo-(dT) groups covalently bound to their surfaces are added, and the material is incubated for another 5 minutes in order to capture the hybrid complexes via the tails of the capture probes.
(4) The paramagnetic particles are washed twice in 2M GuSCN at 37° C., twice in 0.3M KCl, and finally once in a low-salt buffer, which releases the probe-target-capture probe complexes from the oligo-(dT) groups.
(5) The liquid phase is transferred to another vessel containing the first probe, the ribozyme ligase (non-tethered) and ligation buffer (LB) which contains: 30 mM Tris-HCl, pH 7.5, 10 mM $NH_4Cl$, 20 mM $MgCl_2$, 4 mM spermidine. Ligation of those probes that bound to targets proceeds for 2 hours at 58° C. to form amplifiable reporter molecules.
(6) Fresh paramagnetic particles containing short oligo-(dT) tails on their surfaces are added, the GuSCN concentration is raised to 2M, and the material is incubated for another 5 minutes in order to recapture the ligated complexes via the capture probes.
(7) The paramagnetic particles are washed twice in 2M GuSCN at 37° C., twice in 0.3M KCl, and finally once in a low-salt buffer, which releases the ligated probes-target-capture probe complexes from the oligo-(dT) groups.
(8) Qβ replicase is added, and a 25 minute incubation at 37° C. in the presence of propidium iodide (0.5 μg/ml) is carried out to replicate exponentially the ligated RNA reporter molecules. The reaction is stopped with 40 mM EDTA, and fluorescence is measured in a suitable fluorescence monitor such as a Millipore Cytofluor.

EXAMPLE 4

This embodiment is a nucleic acid sandwich hybridization assay for HIV-1 RNA employing "first probe" and "second probe" as described in Example 2. The ligase sequence used is the Tetrahymena ribozyme ligase of Doudna & Szostak (1989), also as described in Example 2.

This assay is a preferred embodiment. It utilizes the improved technique disclosed in Tyagi et al. U.S. application Ser. No. 08/006,073. That technique includes the use of a separate DNA capture probe and the cleavage of reporter probe-target hybrids (in this case ligated binary probes hybridized to target HIV-1 RNA) from the capture probes with ribonuclease H.

The protocol for this particular assay, depicted in simplified form in FIG. 1, is as follows:

(1) Blood containing HIV-1-infected cells containing HIV RNA target 2 having target sequence 3 is dissolved in 40 μl of 5M GuSCN and 80 mM EDTA. After lysis a 60 μl solution containing tethered ribozyme ligase 4 and second probe 5, as well as suitable biotinylated capture probe 6 capable of binding the RNA target 2 at sequence 7, is added. Tethered ribozyme ligase 4 includes ribozyme ligase sequence 8, holdfast 9, which is capable of hybridizing to target 2 at sequence 10, and short tether sequence 11. Probe 5 contains probe sequence 12 terminating (on the left in FIG. 1) in a guanosine nucleotide, and Qβ replicase template portion 13. Capture probe 6 contains probe sequence 14, spacer 15 and terminal biotin moiety 16.

(2) The mixture is incubated for a period of 30 minutes at 37° C. to allow solution hybridization to proceed.

(3) Paramagnetic particles 17 containing streptavidin 18 on their surfaces are added, and the material is incubated for 8 minutes in order to capture the hybrid complexes via the biotinylated capture probes.

(4) Paramagnetic particles 17 are washed twice with 2M GuSCN at 37° C., twice with 0.3M KCl, and finally twice in ligation buffer (30 mM Tris-HCl, pH 7.5, 10 mM NH$_4$Cl, 20 mM MgCl$_2$, 4 mM spermidine).

(5) A solution containing ligation buffer as well as first probe 19 is added and ligation proceeds for 2 hours at 58 degrees centigrade. Probe 19 contains probe section 20 hybridizable to target sequence 3, and Qβ replicase template portion 21. The ribozyme ligase sequence 8 of tethered ribozyme ligase 4 can reach the ligation point at the juncture of probes 5 and 19.

(6) The particles are washed twice with buffer containing 100 mM KCl, 1 mM EDTA, and finally with release buffer (30 mM Tris-HCl, pH 7.8, 10 mM MgCl$_2$). Then the enzyme ribonuclease H is added (in release buffer), and the solution is incubated for 15 minutes at 37° C. to cleave the target RNA at the site where it is bound to the capture probe, thus releasing the ligated probes-target hybrids (or complexes) 22 from the paramagnetic particles 17.

(7) Qβ replicase is added, and a 25 minute incubation at 37° C. in the presence of propidium iodide (0.5 μg/ml) is carried out to replicate exponentially the ligated RNA probes, i.e., reporter molecule 23. The reaction is stopped with 40 mM EDTA, and fluorescence is measured.

EXAMPLE 5

This embodiment is a preferred nucleic acid hybridization assay for HIV-1 RNA employing the first probe, second probe and tethered Tetrahymena ligase described in Example 2. It utilizes the improved background-reduction techniques of Tyagi et al. Ser. No. 08/006,073 in a protocol different from Example 4 above.

Figure 2:
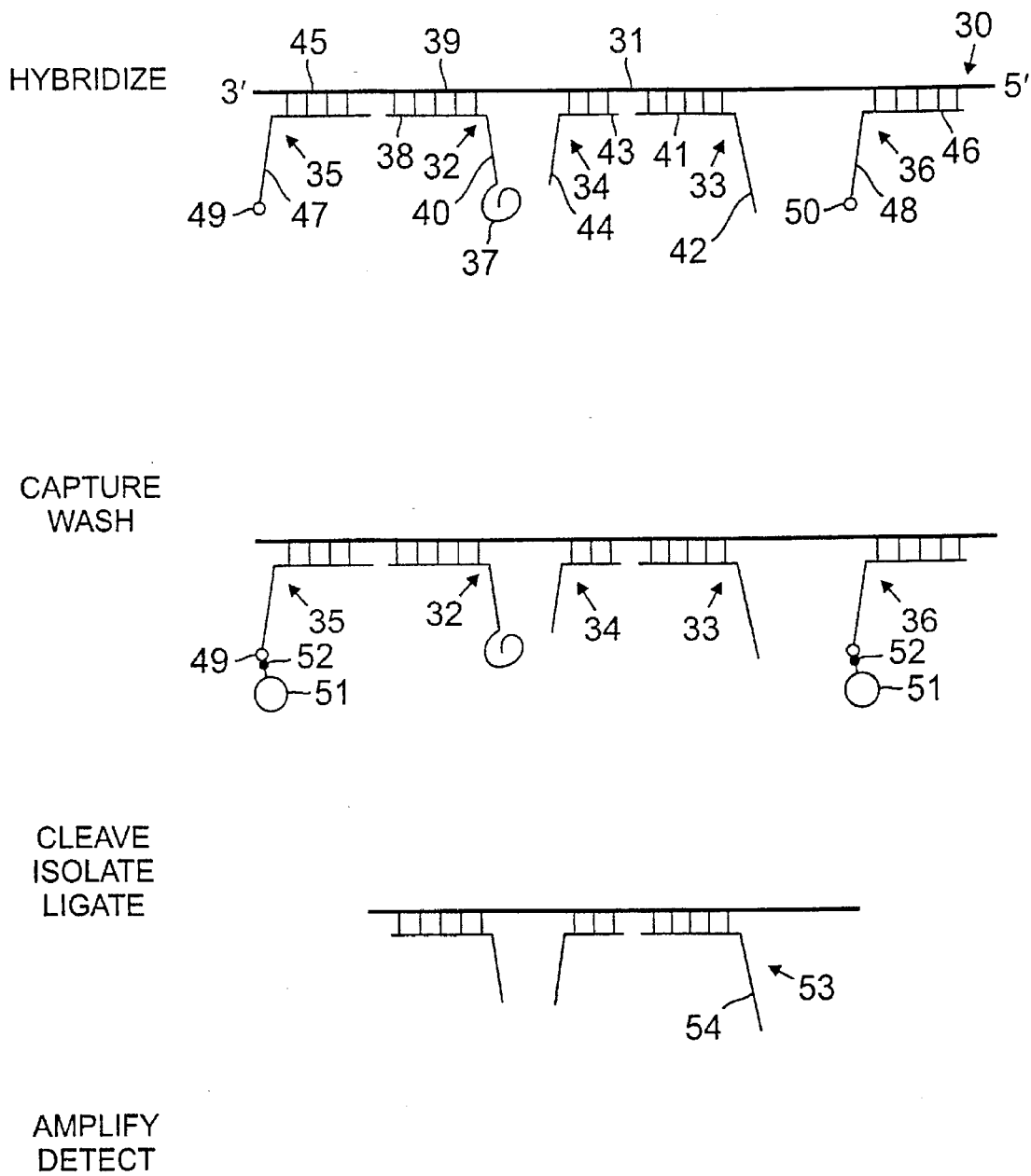
FIG. 2 depicts the assay of Example 5.

The protocol for this particular assay, depicted in simplified form in FIG. 2, is as follows:

Blood containing HIV-1-infected-cells containing HIV RNA target 30 having target sequence 31 is dissolved in 20 μl of 5M guanidine thiocyanate. Then a solution containing tethered ribozyme ligase 32, second probe 33 and first probe 34, as well as a two biotinylated capture probes 35, 36 is added, with sufficient water to reduce the GuSCN concentration to 1M, i.e., an 80-μl solution. The solution contains $10^{13}$ copies of each capture probe, and $2 \times 10^{10}$ copies of each reporter probe and $2 \times 10^{10}$ copies of the tethered ribozyme ligase.

Tethered ribozyme ligase 32 includes ribozyme ligase sequence 37, holdfast 38, which is capable of hybridizing to target 30 at sequence 39, and short tether sequence 40. Probe 33 contains probe sequence 41 terminating (on the left in FIG. 2) in a guanosine nucleotide, and Qβ replicase template portion 42. Probe 34 contains probe sequence 43 and Qβ replicase template portion 44.

The capture probes 35, 36 (SEQ ID NOS. 11–12) used in this example (FIG. 3) have three functional parts. A head 45, 46 of 40–50 nucleotides which hybridize to the preselected target, a spacer 47, 48 of about 4 nucleotides, and a tail 49, 50 that binds tightly to the solid surface. We chose the tail to be a biotin moiety and covalently linked it to the 5' end of each capture probe. The biotin moiety can be attached anywhere in the capture probe, including at the 3' end and internally. The tail can be made up of some other affinity reagent, such as a homopolynucleotide.

FIG. 2 shows the manner in which capture probes 35, 36 (SEQ ID NOS: 11–12) bind to target 30. Two different capture probes were used, rather than one, in order to increase the efficiency of capture and increase the stringency of release of the binary probe-target complexes. The two capture probes 35, 36 (SEQ ID NOS: 11–12) bind to target 30 on either side of the target sequence 31 to which the binary probes bind. Hybridization sequence 45 of capture probe 35 (SEQ ID NO: 11) is complementary to region 4415–4458 of HIV genomic RNA, and hybridization sequence 46 of capture probe 36 (SEQ ID NO: 12) is complementary to region 4808–4852 of HIV genomic RNA. FIG. 3 shows the sequences of the two capture probes 35, 36 (SEQ ID NOS: 11–12) used in this example. Underlines indicate hybridization sequences 45, 46 that are complementary to the target RNA. Both of the capture probes were prepared on a DNA synthesizer.

Hybridization is carried out by incubation at 37 degrees centigrade for one hour. A 30-microliter suspension of paramagnetic particles 51 coated with streptavidin 52 (Promega) is then added to this hybridization mixture. If the capture probes have homopolynucleotide tails, the particles should have a coating of covalently linked complementary oligonucleotides. The probes-target-ligase hybrids are captured on the surface of the paramagnetic particles by a 10-minute incubation at 37 degrees centigrade. The particles are washed with 1M GuSCN four times, with 300 mM KCl three times, and finally with ribozyme ligase buffer (10 mM NH$_4$Cl, 20 mM MgCl$_2$, 4 mM spermidine and 30 mM Tris-HCl, pH 7.4) two times. After washing, one unit of E. coli RNase H (Pharmacia) dissolved in 50 microliters of ribozyme ligase buffer is added. The binary probes-target-ligase hybrids 53 are released from the surface of the paramagnetic particle by a 10-minute incubation at 37 degrees centigrade. The tube containing the mixture is placed in the magnetic field provided by a magnetic separation device to draw the paramagnetic particles 51 to the walls of the test tube. The supernatant is then separated from the paramagnetic particles by aspiration and placed into a fresh tube. The probes-target-ligase hybrids 53 are then incubated for 60 minutes at 58° C. (Doudna & Szostak, 1989) to ligate the binary probes in a target-dependent fashion.

The reporter molecules 54, comprising ligated binary probes, are then amplified by incubation with Qβ replicase. It is not necessary to melt apart the reporter molecule-target hybrids prior to amplification. A mixture containing all of the components of the replication reaction is added. The final reaction mixture (120 microliters) is 45 mM Tris-HCl (pH 8), 10 mM $MgCl_2$, 400 micromolar ATP, 400 micromolar GTP, 400 micromolar UTP, 400 micromolar alpha-$P^{32}$-CTP, and contains 50 micrograms per milliliter Qβ replicase. The reaction is incubated at 37 degrees centigrade for 31 minutes. The sample is mixed with a 45-microliter stop solution (120 mM NaCl, 20 mM EDTA, and 3 microgram per ml proteinase K). This solution stops replication by sequestering the required magnesium ions. The RNA in the stopped reaction is separated from the unincorporated nucleoside triphosphates by precipitating the RNA in an acidic solution (360 mM phosphoric acid, 20 mM sodium pyrophosphate, and 2 mM EDTA), trapping the precipitate on a blotting membrane (Zeta Probe, Biorad), and then washing the membrane with the acidic solution. The RNA on the blots is visualized by autoradiography.

EXAMPLE 6

Figure 4:
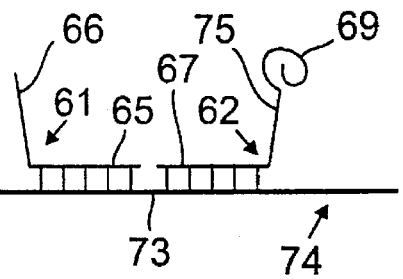
FIG. 4 shows the assay of Example 6.
Figure 4:
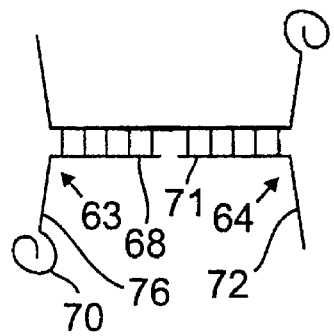
Figure 4:
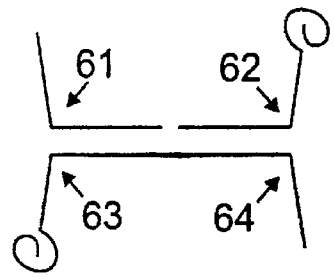

We have devised a novel ligase chain reaction that is different in several important respects from the LCR described by Barany (1991). This assay, including the four RNA LCR probes to be used, is depicted in simplified form in FIG. 4.

The composition of the four probes 61, 62, 63, 64 is as follows: probe 61 is an RNA molecule containing a probe sequence 65 of 9 nucleotides complementary to the sequence of the target region; it may optionally contain additional nucleotides 66 that are not complementary to the target region 93 of target 74. Probe 62 is an RNA molecule which can be 100 to 350 nucleotides in length. The first nucleotide at the 5' end of this probe can be either a guanosine or a 2-amino-purine. The next 9 nucleotides at the 5'-end of this molecule is a probe sequence 67 that is complementary to the 9 nucleotides of target region 73. Probe region 67 is linked to a ribozyme ligase sequence 69, derived from a group I intron, such as the Tetrahymena ribozyme ligase described by Doudna & Szostak (1989), by a tether sequence 75. Probe 63 is an RNA molecule containing 100 to 350 nucleotides; it contains at the 5'-end a guanosine or a 2-amino-purine, followed by probe sequence 68 of 9 nucleotides that is complementary to probe sequence 65 of probe 61. Probe 63 includes the sequence 70 of a ribozyme ligase derived from a group I intron, such as the Tetrahymena ribozyme ligase described by Doudna & Szostak (1989). Probe region 68 is linked to ribozyme sequence 70 by a tether sequence 76. Probe 64 is an RNA molecule containing a probe sequence 71 of 9 nucleotides that are complementary to probe region 67 of probe 62. Probe 64 may optionally contain additional nucleotides 72 that are not complementary to the target sequence.

Probe 61 RNA is generated by in vitro transcription of an artificial gene that codes for the desired RNA sequence and contains a T7 promoter. The gene is purchased from commercial sources as synthetic DNA. Probe 61 comprises 20 nucleotides of RNA such that the last (3'-terminal) 9 nucleotides anneal with a target sequence 73, while 11 nucleotides remain unpaired. Probe 62 RNA is generated by in vitro transcription of an artificial gene that codes for the desired RNA sequence and contains a T7 promoter. The gene is generated by a polymerase chain reaction (Erlich et al., 1991) using plasmid pJD1100 described by Doudna & Szostak (1989). The first PCR primer contains the T7 promoter sequence followed by a guanosine, followed by a 9-nucleotide probe sequence, followed by a 10-nucleotide spacer, and followed by a 15-nucleotide sequence complementary to the 5' end of the ribozyme sequence in the plasmid. The second primer is complementary to the 3' end of the ribozyme sequence.

Probe 63 RNA is generated by in vitro transcription of an artificial gene that codes for the desired RNA sequence and contains a T7 promoter. The gene is generated by a polymerase chain reaction using plasmid pJD1100. The first PCR primer contains the T7 promoter sequence followed by a guanosine, followed by a 9-nucleotide probe sequence followed by a 10-nucleotide spacer, and followed by a 15-nucleotide sequence complementary to the 5' end of the ribozyme sequence in the plasmid. The second primer is complementary to the 3' end of the ribozyme sequence. Probe 64 RNA is generated by in vitro transcription of an artificial gene that codes for the desired RNA sequence and contains a T7 promoter. The gene is purchased from commercial sources as synthetic DNA. Probe 64 comprises 19 nucleotides such that the last (3'-terminal) 9 nucleotides 71 anneal with probe sequence 67 of probe 62, while the remaining 10 nucleotides 72 are unpaired.

In the tethered ligase chain reaction (TLCR) all four LCR probes are incubated with the sample. Initially, probe 61 and probe 62 bind to RNA target 74 under annealing conditions (58° C.), and they are subsequently ligated at a temperature of 58° C. by the ribozyme ligase sequence 69 of probe 62. The resulting hybrid is melted at high temperature (96° C.), and the RNA strand resulting from the ligation of probes 61 and 62 is now able to serve as a template for the annealing of probes 63 and 64, which is carried out by reducing the temperature to 58° C. Ligation is carried out at 58° C., but this time either of the two ligase sequences 69, 70 may catalyze the reaction. Temperature cycling in this case thus requires alteration between only two temperatures, 96° C. for melting and 58° C. for annealing and ligation.

The protocol for this particular TCLR assay, illustrated for HIV-1 RNA target, using the target-purification procedure of Tyagi et al., cited above, is as follows:

Target RNA is purified by-capture, washing, cleaving and isolation according to the procedure described above in Example 5, but in this case no reporter probes are present.

(1) Blood containing HIV-1 infected cells is dissolved in 40 μl of 5M GuSCN and 80 mM EDTA. After lysing a 60 μl solution containing suitable biotinylated capture probes capable of binding the RNA target 74 is added.

(2) The mixture is incubated for a period of 30 minutes at 37° C. to allow solution hybridization to proceed.

(3) Paramagnetic particles containing streptavidin on their surfaces are added, and the material is incubated for 5 minutes in order to capture the target-capture probe hybrids via the biotinylated capture probes.

(4) The paramagnetic particles are washed twice in 2M GuSCN at 37° C., twice with buffer containing 0.3 mM KCl, 1 mM EDTA, and finally with release buffer (30 mM Tris-HCl, pH 7.6, 15 mM $MgCl_2$). Then the enzyme ribonuclease H is added (dissolved in release buffer), and the resulting solution is incubated for 15 minutes at 37° C. to cleave the target RNA sequence bound by the capture probe, thus releasing purified target 73 from the target-capture probe hybrids.

(5) A solution containing probes 61 and 64, as well as ribozyme ligase-tethered probes 62 and 63 (FIG. 3) in ribozyme ligase buffer (30 mM Tris-HCl, pH 7.5, 10 mM $NH_4Cl$, 20 mM $MgCl_2$ and 4 mM spermidine) is added to the purified target 73. The material is annealed and ligated for 15 minutes at 58° C., and melted for 45 seconds at 96° C. in a temperature-cycling instrument. The temperature is cycled 25 times between 58° C. and 96° C. to yield exponential amplification of the RNA target sequence 73. The amplified RNA is then incubated at 96° C. for two minutes to denature the ligated material.

(6) The amount of amplified RNA is determined by polyacrylamide gel electrophoresis.

LITERATURE CITED

Barany, F., Genetic Disease Detection and DNA Amplification Using Cloned Thermostable Ligase. Proc. Natl. Acad. Sci. (USA), 1991; 88:189–193.

Doudna, J. A., Szostak, J. W., RNA-Catalyzed Synthesis of Complementary-Strand RNA. Nature, 1989; 339:519–522.

Doudna, J. A., Couture, S., Szostak, J. W., A Multisubunit Ribozyme That is a Catalyst of and Template for Complementary Strand RNA Synthesis. Science, 1991; 251:1605–1608.

Erlich, H. A., Gelfand, D., and Sninsky, J. J., Recent Advances in the Polymerase Chain Reaction. Science, 1991; 252:1643–1651.

Green, R., Ellington, A., Szostak, J. W., In Vitro Genetic Analysis of the Tetrahymena Self-Splicing Intron. Nature, 1990; 347:406–408.

Green, R. and Szostak, J. W., Selection of a Ribozyme that Functions as a Superior Template in a Self-Copying Reaction. Science, 1992; 258:1910–1915.

Hunsaker, W. R., Badri, H., Lombardo, M. and Collins, M. L., Nucleic Acid Hybridization Assays Employing dA-Tailed Capture Probes. II. Advanced Multiple Capture Methods. Anal. Biochem., 1989; 181:360–370.

Landegren, U., Kaiser, R., Sanders, J., Hood, L., A Ligase-Mediated Gene Detection Technique. Science, 1988; 241:1077–1080.

Landegren, U., and Hood, L. (1991) Method of Detecting a Nucleotide Change in Nucleic Acids. U.S. Pat. No. 4,988,617.

Lizardi, P. M., Guerra, C. E., Lomeli, H., Tussie-Luna, I., Kramer, F. R., Exponential Amplification of Recombinant-RNA Hybridization Probes. Biotechnology, 1988; 6:1197–1202.

Lomeli, H., Tyagi, S., Pritchard, C., Lizardi, P. M., Kramer, F. R., Quantitative Assays Based on the Use of Replicatable Hybridization Probes. Clinical Chemistry, 1989; 35:1826–1381.

Martinelli, R. M. Donahue. J. J. and Unger, J. T., Amplification of Midivariant DNA Templates. European Patent Application Publication Number 0 481 704 A1 (1992).

Michel, F., Hanna, M., Green, R., Bartel, P. P., and Szostak, J. W., The Guanosine Binding Site of the Tetrahymena Ribozyme. Nature 989; 342:391–395.

Morrissey, D. V., Lombardo. M., Eldridge. J. K., Kearney. K. R., Goody, E. P. and Collins. M. L., Nucleic Acid Hybridization Assays Employing dA-Tailed Capture Probes: I. Multiple Capture Methods. Anal. Biochem. 1989; 81:345–359.

Pritchard, C. F., Stefano, J. E., Amplified Detection of Viral Acid at Subattomole Levels Using Qβ Replicase. Ann. Biol. Clin. (Paris), 1990; 48:492–497.

Pritchard, C. F., and Stefano, J. E. (1991) Detection of Viral Nucleic Acids of Qβ Replicase Amplification. Medical Virology 10 (de la Maza, L. M., and Peterson, E. M., eds), pp. 67–80, Plenum Press, New York.

---

We claim:

1. A nucleic acid hybridization assay to detect the presence or absence in a sample containing a heterogeneous mixture of nucleic acid strands of at least one RNA target strand containing a preselected target sequence, comprising the steps of:

a) providing binary probe comprising a first probe of RNA and a second probe of RNA,
      said first probe having at its 3' terminus a first probe sequence of 9–11 nucleotides complementary to a first portion of the preselected target sequence,
      said second probe having a 5'-terminal purine nucleotide and immediately adjacent thereto a second probe sequence of at least 12 nucleotides complementary to a second portion of the target sequence immediately adjacent said first portion,
      said first and second probe sequences being of unequal length and having a combined length of 24 to about 45 nucleotides, b) incubating the sample with said binary probe to form, if said preselected target sequence is present in the sample a binary probe-target sequence hybrid, c) incubating the binary probe-target sequence hybrid from step b with a stringent ribozyme ligase under reaction conditions suitable for stringent, target sequence-directed ligation, for ligating said binary probe in a stringent, target sequence-directed manner to form a reporter molecule, and d) detecting for the reporter molecule as an indication of the presence or absence of the target sequence in the sample.

2. An assay according to claim 1, wherein said reporter molecule is a template for an RNA directed RNA polymerase, and wherein said step of detecting includes amplifying said reporter molecule with an RNA-directed RNA polymerase to produce an amplified product and detecting for said product as an indication of the presence or absence of the target sequence in the sample.

3. An assay according to claim 1, wherein the ligase is a tethered ribozyme ligase comprising a ribozyme sequence linked to one of said first and second probes by a tether.

4. An assay according to claim 1, wherein the ligase is a tethered ribozyme ligase comprising a ribozyme sequence linked by a tether to a holdfast complementary to the target at a site different from the target sequence.

5. An assay according to claim 4 wherein the ribozyme ligase is Tetrahymena ribozyme ligase.

6. An assay according to claim 1 wherein the ribozyme ligase is Tetrahymena ribozyme ligase.

7. A ligase chain reaction nucleic acid hybridization assay to detect the presence or absence in a sample containing a heterogeneous mixture of nucleic acid strands of at least one RNA target strand containing a preselected target sequence, comprising the steps of:

a) providing the sample with a first binary ligase chain reaction probe and a second binary ligase chain reaction probe, said first binary probe comprising a first probe of RNA and a second probe of RNA, said first probe having at its 3+ terminus a first probe sequence of 9–11 nucleotides complementary to a first portion of the preselected target sequence, said second probe having a 5'-terminal purine nucleotide and immediately adjacent thereto a second probe sequence of at least 12 nucleotides complementary to a second portion of the preselected target sequence immediately adjacent said first portion, said first and second probe sequences being of unequal length and having a combined length of 24 to about 45 nucleotides, said second binary probe comprising a third probe of RNA and a fourth probe of RNA, said third probe having at its 3' terminus a third probe sequence of 9–11 nucleotides complementary to a first portion of said probe sequences of said first binary probe, said fourth probe having a 5'-terminal purine nucleotide and immediately adjacent thereto a fourth probe sequence of at least 12 nucleotides complementary to a second portion of said probe sequences of said first binary probe, said second portion being immediately adjacent to said first portion of said probe sequences of said first binary probe, said third and fourth probe sequences being of unequal length and having a combined length of the same number of nucleotides as said probe sequences of said first binary probe, b) incubating said sample with said first and second binary probes, c) incubating the sample with a stringent ribozyme ligase under reaction conditions suitable for stringent, target sequence-directed ligation, for ligating said first binary probes in a stringent, target sequence-directed manner to form a first reporter molecule, and for ligating said second binary probe in a stringent, target sequence-directed manner to form a second reporter molecule, d) incubating the sample at a melting temperature, e) cycling the sample through steps b, c and d twenty or more times, and f) detecting for at least one of said first and second reporter molecules as an indication of the presence or absence of the target sequence in the sample.

8. An assay according to claim 7, wherein the ligase is added in step a).

9. An assay according to claim 8, wherein the hybridization and ligation incubations are performed during the same incubation periods at a single temperature.

10. An assay according to claim 7, wherein the ligase is Tetrahymena ribozyme ligase.

11. An assay according to claim 7, wherein the ribozyme comprises a ribozyme ligase sequence covalently linked to one of said first and second probes by means of a first tether and a ribozyme ligase sequence covalently linked to one of said third and fourth probes by means of a second tether.

12. An assay according to claim 11, wherein the ligase is Tetrahymena ribozyme ligase.

13. An assay according to claim 11, wherein prior to step a, the sample is prepared by isolating the target by means of at least one capture probe.

14. An assay according to claim 13, wherein said at least one capture probe is DNA, and wherein the sample is prepared by incubation with ribonuclease H.

15. An assay according to claim 14, wherein said ligase is Tetrahymena ribozyme ligase.

16. A nucleic acid hybridization assay to detect the presence or absence in a sample containing a heterogenous mixture of nucleic acid strands of at least one RNA target strand containing a preselected target sequence, comprising the steps of:

a) providing binary probe comprising a first probe of RNA and a second probe of RNA, said first probe having at its 3' terminus a first probe sequence of 9–11 nucleotides complementary to a first portion of the preselected target sequence, said second probe having a 5'-terminal purine nucleotide and immediately adjacent thereto a second probe sequence of at least 12 nucleotides complementary to a second portion of the target sequence immediately adjacent said first portion, said first and second probe sequences being of unequal length and having a combined length of 24 to about 45 nucleotides, b) incubating the sample with said first probe and incubating said sample with a capture probe to form, if said preselected target sequence is present in the sample, capture probe-target sequence-first probe hybrids, c) immobilizing the capture probe on a surface of a solid, d) washing the solid, e) incubating the washed solid with said second probe to form capture probe-target sequence-first probe-second probe hybrids, f) incubating the hybrids from step e with a stringent ribozyme ligase under conditions suitable for stringent target sequence-directed ligation, for ligating said binary probe in a target sequence-directed manner to form a reporter molecule, g) separating hybrids containing said reporter molecule from non-ligated second probe, h) amplifying said reporter molecule with an RNA-directed RNA polymerase to produce an amplified product, and i) detecting for said amplified product as an indication of the presence or absence of the target sequence in the sample.

17. An assay according to claim 16, wherein said RNA polymerase is Qβ replicase.

18. An assay according to claim 17, wherein said ligase is Tetrahymena ribozyme ligase.

19. An assay according to claim 16, wherein the step of ligating is performed with the ligase that is not a tethered ligase.

20. An assay according to claim 16, wherein the ligase is a tethered ribozyme ligase comprising a ribozyme sequence linked to a holdfast complementary to the target at a site different from the target sequence by a tether and wherein the tethered ribozyme ligase is added at one of steps a), d) and e).

21. An assay according to claim 20, wherein said ligase is Tetrahymena ribozyme ligase.

22. An assay according to claim 20, wherein said RNA polymerase is Qβ replicase.

23. An assay according to claim 16, wherein said step of separating includes immobilization of said capture probes via their tails not hybridized to the target.

24. A kit of reagents for performing a binary probe hybridization assay to detect the presence or absence in a sample containing a heterogeneous mixture of nucleic acid strands of at least one RNA target strand containing a preselected target sequence comprising:

a) binary probe comprising a first probe of RNA and a second probe of RNA, said first probe having at its 3' terminus a first probe sequence of 9–11 nucleotides complementary to a first portion of the preselected target sequence, said second probe having a 5'-terminal purine nucleotide and immediately adjacent thereto a second probe sequence of at least 12 nucleotides complementary to a second portion of the target sequence immediately adjacent said first portion, said first and second probe sequences being of unequal length and having a combined length of 24 to about 45 nucleotides, b) a stringent ribozyme ligase for ligating said binary probe in a target sequence-directed manner, and c) instructions.

25. A kit of reagents according to claim 24, wherein said first and second probes, when ligated, form a reporter molecule that is exponentially amplifiable by an RNA-directed RNA polymerase.

26. A kit according to claim 25 further comprising Qβ replicase.

27. A kit according to claim 24 wherein said ligase is attached to an extender through which the ligase may be tethered to the target by hybridization to a site outside of the target sequence.

28. A kit according to claim 24, wherein the ligase is Tetrahymena ribozyme ligase.

29. A kit according to claim 28 further comprising a capture probe.

30. A kit according to claim 24 further comprising a capture probe.

31. A kit of reagents for performing a tethered ligase chain reaction assay to detect the pressure or absence in a sample containing a heterogeneous mixture of nucleic acid strands of at least one RNA target strand containing a preselected target sequence, comprising:

a) a first binary ligase chain reaction probe comprising a first probe of RNA and a second probe of RNA, said first probe having at its 3' terminus a first probe sequence of 9–11 nucleotides complementary to a first portion of the preselected target sequence, said second probe having a 5'-terminal purine nucleotide and immediately adjacent thereto a second probe sequence of at least 12 nucleotides complementary to a second portion of the target sequence immediately adjacent said first portion, said first and second probe sequences being of unequal length and having a combined length of 24 to about 45 nucleotides, one of said first and second probes including a first stringent ribozyme ligase covalently linked thereto by an oligonucleotide extender, b) a second binary ligase chain reaction probe comprising a third probe of RNA and a fourth probe of RNA, said third probe having at its 3' terminus a third probe sequence of 9–11 nucleotides complementary to a first portion of said probe sequences of said first binary probe, said fourth probe having a 5'-terminal purine nucleotide and immediately adjacent thereto a fourth probe sequence of at least 12 nucleotides complementary to a second portion of said probe sequences of said first binary probe, said second portion being immediately adjacent said first portion of said probe sequences of said first binary probe, said third and fourth probe sequences being of unequal length and having a combined length of the same number of nucleotides as said probe sequences of said first binary probe, one of said third or fourth probes including a second stringent ribozyme ligase covalently linked thereto by an oligonucleotide extender, and c) instructions.

32. A kit according to claim 31 further comprising a capture probe.

33. A kit according to claim 31 wherein each of said first stringent ribozyme ligase and said second stringent ribozyme ligase is Tetrahymena ribozyme ligase.

34. The kit according to claim 33 wherein said first and second ribozyme ligases are the same ribozyme ligase.

35. An assay according to claim 1 comprising an assay for diagnosis of a disease or condition in humans.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( v i ) ORIGINAL SOURCE:
        ( A ) ORGANISM: Human immunodeficiency virus type 1

( x i ) SEQUENCE DESCRIPTION: SEQ ID NO:1:

```
GGGGACCCCC  CCGGAAGGGG  GGGACGAGGU  GCGGGCACCU  CGUACGGGAG  UUCGAGCUG      60

ACGACCGUAG  U                                                              71
```

( 2 ) INFORMATION FOR SEQ ID NO:2:

( i ) SEQUENCE CHARACTERISTICS:
        ( A ) LENGTH: 186 base pairs
        ( B ) TYPE: nucleic acid
        ( C ) STRANDEDNESS: single (D) TOPOLOGY: linear (ii) MOLECULE TYPE: RNA (genomic)

(iii) HYPOTHETICAL: NO (vi) ORIGINAL SOURCE:
(A) ORGANISM: Human immunodeficiency virus type 1

(xi) SEQUENCE DESCRIPTION: SEQ ID NO:2:

```
GACUGGUGAA  AUUGCUGCCA  UUGUCUGUAG  CACGCGCUAG  CGCUUUCGCG  CUCUCCCAGG    60
UGACGCCUCG  UGAAGAGGCG  CGACCUUCGU  GCGUUUCGGC  AACGCACGAG  AACCGCCACG   120
CUGCUUCGCA  GCGUGGCUCC  UUCGCGCAGC  CCGCUGCGCG  AGGUGACCCC  CCGAAGGGGG   180
GUUCCC                                                                   186
```

(2) INFORMATION FOR SEQ ID NO:3:

(i) SEQUENCE CHARACTERISTICS:
(A) LENGTH: 9 base pairs
(B) TYPE: nucleic acid
(C) STRANDEDNESS: single
(D) TOPOLOGY: linear (ii) MOLECULE TYPE: RNA (genomic)

(iii) HYPOTHETICAL: NO (vi) ORIGINAL SOURCE:
(A) ORGANISM: Human immunodeficiency virus type 1

(xi) SEQUENCE DESCRIPTION: SEQ ID NO:3:

```
GCUACGGUU                                                                  9
```

(2) INFORMATION FOR SEQ ID NO:4:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: RNA (genomic)

(iii) HYPOTHETICAL: NO (vi) ORIGINAL SOURCE:
(A) ORGANISM: Human immunodeficiency virus type 1

(xi) SEQUENCE DESCRIPTION: SEQ ID NO:4:

```
UACAGACAAU  GGCAGCAAUU  UCACCAGU                                          28
```

(2) INFORMATION FOR SEQ ID NO:5:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (xi) SEQUENCE DESCRIPTION: SEQ ID NO:5:

```
TGCGTAATAC  GACTCACTAT  AGACTGGTGA  AATTGCTGCC  ATTGTCTGTA  GCACGCTGCT    60
AGCGCTTTCG  CGCTCTCC                                                      78
```

(2) INFORMATION FOR SEQ ID NO:6:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:6:

```
GGGGAACCCC CCTTCGGGGG GTCACC                                    26
```

( 2 ) INFORMATION FOR SEQ ID NO:7:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:7:

```
GCGTAATACG ACTCACTATA GGGTTTTTAC TGGCCATCTT CCTGCTAATT TTAAGTTGAG    60
AGTTATCAGG CATGCACCTG                                               80
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:8:

```
CTAGCTCCCA TTAAGGAGAG                                           20
```

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:9:

```
GTTTTTACTG GCCATCTTCC TGCTAATTTT AA                             32
```

( 2 ) INFORMATION FOR SEQ ID NO:10:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:10:

TTTGAG                                                                 6

( 2 ) INFORMATION FOR SEQ ID NO:11:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Human immunodeficiency virus type 1

( x i ) SEQUENCE DESCRIPTION: SEQ ID NO:11:

TACGACTGCT ACCAAGATAA CTTTTCCTTC TAAATGTGTA CAATCTAGC                  49

( 2 ) INFORMATION FOR SEQ ID NO:12:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Human immunodeficiency virus type 1

( x i ) SEQUENCE DESCRIPTION: SEQ ID NO:12:

TACGATGTCT GTTGCTATTA TGTCTACTAT TCTTTCCCCT GCACTGTAC                  49